(12) United States Patent
Pelzer et al.

(10) Patent No.: US 12,297,169 B2
(45) Date of Patent: May 13, 2025

(54) 1-ALKOXYETHYL-4-ISOBUTYL-BENZENE AS AROMA INGREDIENTS

(71) Applicant: BASF SE, Ludwigshafen am Rhein (DE)

(72) Inventors: Ralf Pelzer, Lampertheim (DE); Wolfgang Siegel, Ludwigshafen am Rhein (DE); Miriam Bru Roig, Lampertheim (DE); Manuel Danz, Ludwigshafen am Rhein (DE); Silke Weyland, Lampertheim (DE); Florian Garlichs, Lampertheim (DE); Volker Hickmann, Ludwigshafen am Rhein (DE); Melanie Weingarten, Ludwigshafen am Rhein (DE)

(73) Assignee: BASF SE

( * ) Notice: Subject to any disclaimer, the term of this patent is extended or adjusted under 35 U.S.C. 154(b) by 690 days.

(21) Appl. No.: 17/621,736

(22) PCT Filed: Jun. 19, 2020

(86) PCT No.: PCT/EP2020/067215
§ 371 (c)(1),
(2) Date: Dec. 22, 2021

(87) PCT Pub. No.: WO2020/260165
PCT Pub. Date: Dec. 30, 2020

(65) Prior Publication Data
US 2022/0251014 A1    Aug. 11, 2022

(30) Foreign Application Priority Data
Jun. 24, 2019    (EP) .................... 19181997

(51) Int. Cl.
| | | |
|---|---|---|
| *C07C 43/164* | (2006.01) | |
| *A61K 8/33* | (2006.01) | |
| *A61K 47/06* | (2006.01) | |
| *A61Q 13/00* | (2006.01) | |
| *A61Q 15/00* | (2006.01) | |
| *A61Q 19/00* | (2006.01) | |
| *C11B 9/00* | (2006.01) | |
| *C11D 3/20* | (2006.01) | |
| *C11D 3/50* | (2006.01) | |

(52) U.S. Cl.
CPC ............. *C07C 43/164* (2013.01); *A61K 8/33* (2013.01); *A61K 47/06* (2013.01); *A61Q 13/00* (2013.01); *A61Q 15/00* (2013.01); *A61Q 19/00* (2013.01); *C11B 9/0015* (2013.01); *C11D 3/2068* (2013.01); *C11D 3/50* (2013.01)

(58) Field of Classification Search
None
See application file for complete search history.

(56) References Cited

U.S. PATENT DOCUMENTS 5,278,335 A * 1/1994 Chockalingam ........ C07C 67/36
562/406

OTHER PUBLICATIONS

Rajashekharam et al, Kinetics of hydrogenation of p-isobutyl acetophenone using a supported Ni catalyst in a slurry reactor, 1996, Chemical Engineering Science, vol. 51, No. 10, 1663-1672 (Year: 1996).*
Schneider et al, Palladium-catalyzed Alkoxycarbonylation of sec-Benzylic Ethers, 2020, Eur. J. Org. Chem., 932-936 (Year: 2020).*
Bauer et al., "Common Fragrance and Flavor Materials: Preparation and Uses, Fourth, Completely Revised Edition; Chapter 2: Single Fragrance and Flavor Materials", Common fragrance and flavor materials and uses, Dec. 31, 2001, pp. 7-165.
European Search Report for EP Patent Application No. 19181997.8, Issued on Nov. 29, 2019, 3 pages.
International Preliminary Report on Patentability received for PCT Patent Application No. PCT/EP2020/067215, mailed on Jan. 6, 2022, 9 pages.
International Search Report and Written Opinion received for PCT Patent Application No. PCT/EP2020/067215, mailed on Sep. 24, 2020, 10 pages.
Rajashekharam et al., "Improved stability of a bimetallic Ni—Pt catalyst for hydrogenation of acetophenone and substituted derivatives", Catalysis Letters, vol. 41, No. 3-4, Dec. 31, 1996, pp. 171-176.

* cited by examiner

*Primary Examiner* — Jessica Whiteley
(74) *Attorney, Agent, or Firm* — Faegre Drinker Biddle & Reath LLP

(57) ABSTRACT

The presently claimed invention is directed to the use of 1-alkoxyethyl-4-isobutyl-benzene of formula (I) to impart an aroma impression to a composition. The presently claimed invention also relates to a method of imparting such aroma impression. The present invention is further directed to compositions comprising the compound of formula (I) and at least one aroma chemical as well as to compositions comprising the compound of formula (I) and at least one further component selected from the group consisting of aroma chemicals, surfactants, oil components, anti-oxidants, deodorant-active agents and solvents. The present invention also relates to a compound of formula (I').

14 Claims, No Drawings

1-ALKOXYETHYL-4-ISOBUTYL-BENZENE AS AROMA INGREDIENTS

CROSS-REFERENCE TO RELATED APPLICATIONS

This application is a national stage application (under 35 U.S.C. § 371) of PCT/EP2020/067215, filed Jun. 19, 2020, which claims benefit of European Application No. 19181997.8, filed Jun. 24, 2019, both of which are incorporated herein by reference in their entirety.

FIELD OF THE INVENTION

The presently claimed invention is directed to the use of 1-alkoxyethyl-4-isobutyl-benzene of formula (I) to impart an aroma impression to a composition. The presently claimed invention also relates to a method of imparting such aroma impression. The present invention is further directed to compositions comprising the compound of formula (I) and at least one aroma chemical as well as to compositions comprising the compound of formula (I) and at least one further component selected from the group consisting of aroma chemicals, surfactants, oil components, anti-oxidants, deodorant-active agents and solvents. The present invention also relates to a compound of formula (I').

BACKGROUND OF THE INVENTION

Aroma chemicals, especially fragrances, are of great interest in the field of cosmetics and cleaning and laundry compositions. Fragrances of natural origin are mostly expensive, often limited in their availability and, on account of fluctuations in environmental conditions, are also subject to variations in their content, purity etc. To circumvent these undesirable factors, it is therefore of great interest to create synthetic substances which have sensory properties that resemble more expensive natural fragrances, or which have novel and interesting sensory profiles.

Despite a large number of already existing aroma chemicals, there is a constant need for new components in order to be able to satisfy the multitude of properties desired for extremely diverse areas of application. These include, firstly, the sensory properties, i.e. the compounds should have advantageous odiferous (olfactory) or gustatory properties. Furthermore, aroma chemicals should also have additional positive secondary properties, such as e.g. an efficient preparation method, the possibility of providing better sensory profiles as a result of synergistic effects with other aroma chemicals, a higher stability in a wide range of compositions as well as under certain application conditions, a higher extendibility and/or a better staying power.

There is an increased need for aroma chemicals which can impart an aroma impression, especially a flowery and/or a marine and/or a green odiferous impression to a composition. Such properties are of special interest for compositions such as for example body care compositions, hygiene articles, cleaning compositions, textile detergent compositions and compositions for scent dispensers. Of special interest are aroma chemicals, which can impart one or more distinct aroma impressions to a composition, thereby contributing to a rich and interesting sensory profile, especially an olfactory profile of the composition. In addition, especially regarding aroma chemicals which can impart an aroma impression, the substantivity as well as the tenacity are of special interest in order to obtain a long-lasting odiferous impression in the composition as well as to the surface with which the composition is treated.

It is an object of the present invention to provide an aroma chemical, which can impart an aroma impression, a flowery and/or a marine and/or a green and/or a sweet note and/or a rubbery note and/or a nutty note and/or a woody note and/or a dusty note and/or a rooty note and/or a lemon note odiferous impression, to a composition. It is further an object of the present invention to provide an aroma chemical, which can impart a long-lasting aroma impression, especially a flowery and/or a marine and/or a green and/or a sweet note and/or a rubbery note and/or a nutty note and/or a woody note and/or a dusty note and/or a rooty note and/or a lemon note odiferous impression, to a composition as well as to surfaces treated with such compositions, such as for example skin and or textiles and is stable in a wide variety of compositions.

SUMMARY OF THE INVENTION

It was surprisingly found that a compound of formula (I) imparts an aroma impression, especially a flowery and/or a marine and/or a green and/or a sweet note and/or a rubbery note and/or a nutty note and/or a woody note and/or a dusty note and/or a rooty note and/or a lemon note odiferous impression, to a composition. Such an aroma impression is stable in the wide range of compositions and, thus, contributes to a rich and interesting aroma profile of the composition.

Thus, in one aspect the present invention is directed to the use of a compound of formula (I),

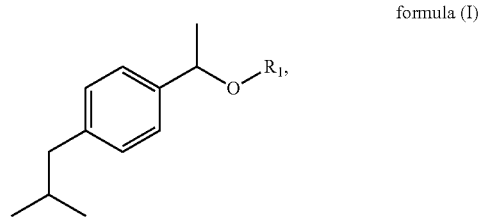

formula (I)

wherein
$R_1$ is selected from the group consisting of linear or branched, unsubstituted —$C_1$-$C_5$ alkyl and unsubstituted —$C_3$-$C_5$ cycloalkyl;
or its salt or stereoisomer thereof,
to impart an aroma impression to a composition.

In another aspect, the present invention provides a method of imparting an aroma impression to a composition comprising at least the step of adding a compound of formula (I),

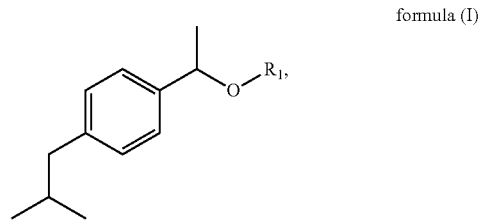

formula (I)

wherein
$R_1$ is selected from the group consisting of linear or branched, unsubstituted —$C_1$-$C_5$ alkyl and unsubstituted —$C_3$-$C_5$ cycloalkyl;

or its salt or stereoisomer thereof,
to a composition.

In yet another aspect, the present invention provides a composition comprising at least one compound of the formula (I),

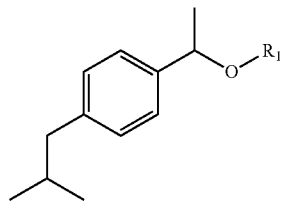

formula (I)

wherein
R$_1$ is selected from the group consisting of linear or branched, unsubstituted —C$_2$-C$_5$ alkyl and unsubstituted —C$_3$-C$_5$ cycloalkyl;
or its salt or stereoisomer thereof and
(i) at least one aroma chemical, or
(ii) at least one non-aroma chemical carrier, or
(iii) both of (i) and (ii).

In yet another aspect, the present invention relates to a mixture comprising compound of formula (I),

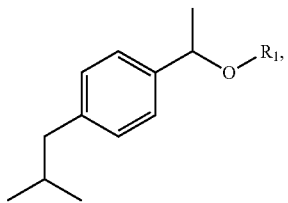

formula (I)

wherein
R$_1$ is selected from the group consisting of linear or branched, unsubstituted —C$_1$-C$_5$ alkyl and unsubstituted —C$_3$-C$_5$ cycloalkyl;
or its salt or stereoisomer thereof; and
4-methyl-2-(2-methylpropyl)oxan-4-ol.

In a further aspect, the present invention relates to the use of the mixture to impart an aroma impression to a composition.

In a further aspect, the present invention relates to a composition comprising,
(i) the mixture
(ii) at least one aroma chemical, or
(iii) at least one non-aroma chemical carrier, or
(iv) both (ii) and (iii).

In yet another aspect, the present invention provides a compound of formula (I'),

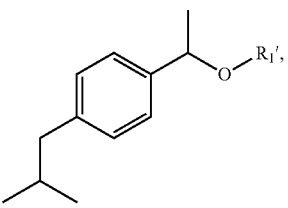

formula (I')

wherein
R$_1$' is selected from the group consisting of linear or branched —CH$_2$CH$_2$CH$_3$, —CH(CH$_3$)(C$_2$H$_5$), —CH$_2$CH(CH$_3$)$_2$ and —CH$_2$CH$_2$CH$_2$CH$_3$;
or its salt or stereoisomer thereof.

DETAILED DESCRIPTION OF THE INVENTION

The following detailed description is merely exemplary in nature and is not intended to limit the presently claimed invention or the application and uses of the presently claimed invention. Furthermore, there is no intention to be bound by any theory presented in the preceding technical field, background, summary or the following detailed description.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

Furthermore, the terms "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the subject matter described herein are capable of operation in other sequences than described or illustrated herein. In case the terms "(A)", "(B)" and "(C)" or AA), BB) and CC) or "(a)", "(b)", "(c)", "(d)", "(i)", "(ii)" etc. relate to steps of a method or use or assay there is no time or time interval coherence between the steps, that is, the steps may be carried out simultaneously or there may be time intervals of seconds, minutes, hours, days, weeks, months or even years between such steps, unless otherwise indicated in the application as set forth herein above or below.

In the following passages, different aspects of the subject matter are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" or "preferred embodiment" means that a particular feature, structure or characteristic described in connection with the embodiment is included in at least one embodiment of the presently claimed invention. Thus, appearances of the phrases "in one embodiment" or "In a preferred embodiment" or "in a preferred embodiment" in various places throughout this specification are not necessarily all referring to the same embodiment but may refer. Furthermore, the features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the subject matter, and form different embodiments, as would be understood by those in the art. For example, in the appended claims, any of the claimed embodiments are used in any combination.

Furthermore, the ranges defined throughout the specification include the end values as well, i.e. a range of 1 to 10 implies that both 1 and 10 are included in the range. For the avoidance of doubt, the applicant shall be entitled to any equivalents according to applicable law.

Definitions

In the context of the present invention, the term "aroma" refers to a sensory property and comprises an odor and/or a flavor.

The term "aroma chemical" denotes a substance which is used to obtain a sensory or organoleptic (used interchangeably herein) impression and comprises its use to obtain an olfactory and/or a flavor impression. The term "olfactory impression" denotes an odor impression without any positive or negative judgement, while the term "scent impression" or "fragrance impression" or "aroma impression" (used interchangeably herein) as used herein is connected to an odor impression which is generally felt as pleasant. Thus a "fragrance" or "scent" denotes an aroma chemical, which predominately induces a pleasant odor impression. A flavor induces a taste impression.

The term "aroma composition", as used herein, refers to a composition which induces an aroma. The term aroma composition comprises "odor composition" and/or "flavor composition". An odor composition being a composition, which predominately induces an odor impression, a flavor composition being a composition, which predominantly induces a taste impression.

The term odor composition comprises "fragrance composition" or "scent composition" (used interchangeably herein), which predominately induce an odor impression which is generally felt as pleasant.

The general hedonistic expressions "advantageous sensory properties" or "advantageous organoleptic properties" describe the niceness and conciseness of an organoleptic impression conveyed by an aroma chemical. "Niceness" and "conciseness" are terms which are familiar to the person skilled in the art, such as a perfumer. Niceness generally refers to a spontaneously brought about, positively perceived, pleasant sensory impression. However, "nice" does not have to be synonymous with "sweet". "Nice" can also be the odor of musk or sandalwood. "Conciseness" generally refers to a spontaneously brought about sensory impression which—for the same test panel—brings about a reproducibly identical reminder of something specific. For example, a substance can have an odor which is spontaneously reminiscent of that of an "apple": the odor would then be concisely of "apples". If this apple odor were very pleasant because the odor is reminiscent, for example, of a sweet, fully ripe apple, the odor would be termed "nice". However, the odor of a typically tart apple can also be concise. If both reactions arise upon smelling the substance, in the example thus a nice and concise apple odor, then this substance has particularly advantageous sensory properties.

The expressions "combination of", "in combination with" or "combined with" when used herein referring to the compositions, methods or the use of two compounds, take account of the fact that the two compounds do not need to be used in the form of a physical mixture of said compounds but can be used (e.g., added) separately. Where the compounds are used separately, they can be used (e.g. added) sequentially (i.e. one after the other) in any order, or concurrently (i.e. basically at the same time).

The term "boosting" or "boost" is used herein to describe the effect of enhancing and/or modifying the aroma of an aroma chemical or of a composition. The term "enhancing" comprises an improvement of the niceness and/or conciseness of an aroma and/or an improvement of the intensity. The term "modifying" comprises the change of an aroma profile.

The intensity can be determined via a threshold value determination. A threshold value of an odor is the concentration of a substance in the relevant gas space at which an odor impression can just still be perceived by a representative test panel, although it no longer has to be defined.

Booster effects are particularly desired in fragrance composition when top-note-characterized applications are required, in which the odor is to be conveyed particularly quickly and intensively, for example in deodorants, air fresheners or in the taste sector in chewing gums.

The terms "the invention relates to" and "the invention is directed to" are used synonymously throughout the invention.

The terms "compound" and "substance" are used synonymously throughout the invention.

The term "tenacity" describes the evaporation behavior over time of an aroma chemical. The tenacity can for example be determined by applying the aroma chemical to a test strip, and by subsequent olfactory evaluation of the odor impression of the test strip. For aroma chemicals with high tenacity the time span after which the panel can still identify an aroma impression is long.

The term "substantivity" describes the interaction of an aroma chemical with a surface, such as for example the skin or a textile, especially after subsequent treatment of the surface, such as for example washing. The substantivity can for example be determined by washing a textile with a textile detergent composition comprising the aroma chemical and subsequent olfactory evaluation of the textile directly after washing (wet textile) as well as evaluation of the dry textile after prolonged storage.

The term "stability" describes the behavior of an aroma chemical upon contact with oxygen, light and/or other substances. An aroma chemical with high stability maintains its aroma profile over a long period in time, preferably in a large variety of compositions and under various storage conditions.

In order to impart a long-lasting aroma impression to a composition or to a surface treated with a composition, the tenacity, the substantivity as well as the stability of the aroma chemical in the compositions should preferably be high.

Use and Method

One embodiment of the invention is directed to a use of a compound of formula (I),

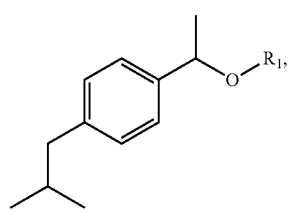

formula (I)

wherein $R_1$ is selected from the group consisting of linear or branched, unsubstituted —$C_1$-$C_5$ alkyl and unsubstituted —$C_3$-$C_5$ cycloalkyl;

or its salt or stereoisomer thereof,
to impart an aroma impression to a composition.

One embodiment of the invention is directed to a method of imparting an aroma impression to a composition comprising at least the step of adding a compound of formula (I),

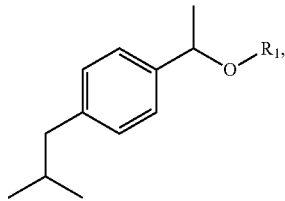

formula (I)

wherein
R$_1$ is selected from the group consisting of linear or branched, unsubstituted —C$_1$-C$_5$ alkyl and unsubstituted —C$_3$-C$_5$ cycloalkyl;
or its salt or stereoisomer thereof,
to a composition.

In a preferred embodiment, R$_1$ is selected from the group consisting of —CH$_3$, —CH$_2$CH$_3$, —CH$_2$CH$_2$CH$_3$, —CH(CH$_3$)$_2$, —CH(CH$_3$)(C$_2$H$_5$), —CH$_2$CH(CH$_3$)$_2$, —CH$_2$CH$_2$CH$_2$CH$_3$ and cyclopropyl, more preferably R$_1$ is selected from the group consisting of —CH$_3$, —CH$_2$CH$_3$, —CH(CH$_3$)$_2$, —CH(CH$_3$)(C$_2$H$_5$) and —CH$_2$CH(CH$_3$)$_2$.

In yet another preferred embodiment, the composition is selected from perfume compositions, body care compositions, hygiene articles, cleaning compositions, textile detergent compositions, compositions for scent dispensers, foods, food supplements, pharmaceutical compositions and crop protection compositions.

In one embodiment, the impression is a flowery note. In one embodiment, the impression is a marine note. In one embodiment, the impression is a green note. In one embodiment, the impression is a sweet note. In one embodiment, the impression is a rubbery note. In one embodiment, the impression is a nutty note. In one embodiment, the impression is a woody note. In one embodiment, the impression is a dusty note. In one embodiment, the impression is a rooty note. In one embodiment, the impression is a lemon note.

In a preferred embodiment, the compound of formula (I) or its salts or stereoisomer is present in an amount in the range of 0.01 wt. % to 70.0 wt. %, more preferably in the range of 0.05 wt. % to 60.0 wt. %, particularly in the range of 0.1 wt. % to 50.0 wt. %, based on the total weight of the composition. In yet another preferred embodiment, the compound of formula (I) or its salts or stereoisomer is present in an amount in the range of 0.05 wt. % to 10 wt. %, more preferably 0.1 wt. % to 5 wt. %, yet more preferably 0.2 wt. % to 3 wt. %, most preferably 20 wt. % to 70 wt. %, particularly 25 wt. % to 50 wt. %, based on the total weight of the composition.

Composition

One embodiment of the presently claimed invention is directed to a composition comprising a at least one compound of the formula (I),

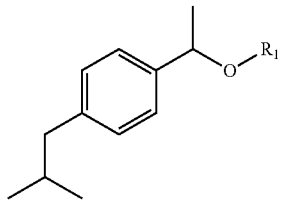

formula (I)

wherein
R$_1$ is selected from the group consisting of linear or branched, unsubstituted —C$_2$-C$_5$ alkyl and unsubstituted —C$_3$-C$_5$ cycloalkyl;
or its salt or stereoisomer thereof and
(i) at least one aroma chemical, or
(ii) at least one non-aroma chemical carrier, or
(iii) both of (i) and (ii).

In a preferred embodiment, R$_1$ is selected from the group consisting of —CH$_2$CH$_3$, —CH$_2$CH$_2$CH$_3$, —CH(CH$_3$)$_2$, —CH(CH$_3$)(C$_2$H$_5$), —CH$_2$CH(CH$_3$)$_2$, —CH$_2$CH$_2$CH$_2$CH$_3$, cyclopropyl and cyclobutyl. In yet another preferred embodiment, R$_1$ is selected from the group consisting of —CH$_2$CH$_3$, —CH$_2$CH$_2$CH$_3$, —CH(CH$_3$)$_2$, —CH(CH$_3$)(C$_2$H$_5$), —CH$_2$CH(CH$_3$)$_2$ and —CH$_2$CH$_2$CH$_2$CH$_3$. In yet another preferred embodiment, R$_1$ is selected from the group consisting of cyclopropyl and cyclobutyl.

In yet another preferred embodiment, the at least one aroma chemical (i) is selected from the group consisting of geranyl acetate, alpha-hexylcinnamaldehyde, 2-phenoxyethyl isobutyrate, dihydromyrcenol, methyl dihydrojasmonate, 4,6,6,7,8,8-hexamethyl-1,3,4,6,7,8-hexahydrocyclopenta[g]benzopyran, tetrahydrolinalool, ethyllinalool, benzyl salicylate, 2-methyl-3-(4-tert-butylphenyl)propanal, cinnamyl alcohol, 4,7-methano-3a,4,5,6,7,7a-hexahydro-5-indenyl acetate and/or 4,7-methano-3a,4,5,6,7,7a-hexahydro-6-indenyl acetate, citronellol, citronellyl acetate, tetrahydrogeraniol, vanillin, linalyl acetate, styrolyl acetate, octahydro-2,3,8,8-tetramethyl-2-acetonaphthone and/or 2-acetyl-1,2,3,4,6,7,8-octahydro-2,3,8,8-tetramethylnaphthalene, hexyl salicylate, 4-tert-butylcyclohexyl acetate, 2-tertbutylcyclohexyl acetate, alpha-ionone, n-alpha-methylionone, alpha-isomethylionone, coumarin, terpinyl acetate, 2-phenylethyl alcohol, 4-(4-hydroxy-4-methylpentyl)-3-cyclohexenecarboxaldehyde, alpha-amylcinnamaldehyde, ethylene brassylate, (E)- and/or (Z)-3-methylcyclopentadec-5-enone, 15-pentadec-11-enolide and/or 15-pentadec-12-enolide, 15-cyclopentadecanolide, 1-(5,6,7,8-tetrahydro-3,5,5,6,8,8-hexamethyl-2-naphthalenyl)ethanone, 2-isobutyl-4-methyltetrahydro-2H-pyran-4-ol, 2-ethyl-4-(2,2,3-trimethyl-3-cyclopenten-1-yl)-2-buten-1-ol, cis-3-hexenyl acetate, trans-3-hexenyl acetate, trans-2/cis-6-nonadienol, 2,4-dimethyl-3-cyclohexenecarboxaldehyde, 2,4,4,7-tetramethyloct-6-en-3-one, 2,6-dimethyl-5-hepten-1-al, borneol, 3-(3-isopropylphenyl)butanal, 2-methyl-3-(3,4-methylenedioxyphenyl)propanal, 3-(4-ethyl phenyl)-2,2-dimethylpropanal, 7-methyl-2H-1,5-benzodioxepin-3(4H)-one, 3,3,5-trimethylcyclohexyl acetate, 2,5,5-trimethyl-1,2,3,4,4a,5,6,7-octahydronaphthalen-2-ol, 3-(4-tert-butylphenyl)-propanal, ethyl 2-methylpentanoate, ethoxymethoxycyclododecane, 2,4-dimethyl-4,4a,5,9b-tetrahydroindeno[1,2-d][1,3]dioxine, (2-tert-butylcyclohexyl) acetate and 3-[5,5,6-trimethylbicyclo[2.2.1]hept-2-yl]cyclohexan-1-ol.

In yet another preferred embodiment, the at least one aroma chemical (i) is selected from the group consisting of methyl benzoate, benzyl acetate, geranyl acetate, 2-isobutyl-4-methyltetrahydro-2H-pyran-4-ol, linalool, 2-isobutyl-4-methyltetrahydro-2H-pyran-4-ol and methyl benzoate.

In yet another preferred embodiment, the at least one aroma chemical (i) is selected from the group consisting of ethylvanillin, vanillin, 2,5-dimethyl-4-hydroxy-2H-furan-3-one (furaneol) or 3-hydroxy-2-methyl-4H-pyran-4-one (maltol).

Further aroma chemicals with which the compound of formula (I) can be combined to give a composition according to the presently claimed invention can be found, e.g., in S. Arctander, Perfume and Flavor Chemicals, Vol. I and II, Montclair, N. J., 1969, self-published or K. Bauer, D. Garbe and H. Surburg, Common Fragrance and Flavor Materials, 4th Ed., Wiley-VCH, Weinheim 2001. Specifically, mention may be made of:

extracts from natural raw materials such as essential oils, concretes, absolutes, resins, resinoids, balsams, tinctures such as e.g.

ambergris tincture; amyris oil; angelica seed oil; angelica root oil; aniseed oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; Eau de brouts absolute; oak moss absolute; elemi oil; tarragon oil; *Eucalyptus citriodora* oil; eucalyptus oil; fennel oil; pine needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calmus oil; camomile oil blue; roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; *Litsea cubeba* oil; laurel leaf oil; mace oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; origanum oil; palmarosa oil; patchouli oil; perilla oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; styrax oil; tagetes oil; fir needle oil; tea tree oil; turpentine oil; thyme oil; tolubalsam; tonka absolute; tuberose absolute; vanilla extract; violet leaf absolute; verbena oil; vetiver oil; juniper berry oil; wine lees oil; wormwood oil; winter green oil; hyssop oil; civet absolute; cinnamon leaf oil; cinnamon bark oil, and fractions thereof, or ingredients isolated therefrom;

individual fragrances from the group of hydrocarbons, such as e.g. 3 carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane; the aliphatic alcohols such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1 octen-3-ol; mixture of 3,4,5,6,6-pentamethyl-3/4-hepten-2-ol and 3,5,6,6-tetramethyl-4-methylene-heptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10 trimethyl-5,9-undecadienal; heptanal diethylacetal; 1,1-dimethoxy-2, 2,5 trimethyl-4-hexene; citronellyloxyacetaldehyde; (E/Z)-1-(1-methoxypropoxy)-hex-3-ene; the aliphatic ketones and oximes thereof such as e.g. 2-heptanone; 2-octanone; 3-octanone; 2-nonanone; 5-methyl-3-heptanone; 5-methyl-3 heptanone oxime; 2,4,4,7-tetramethyl-6-octen-3-one; 6-methyl-5-hepten-2-one;

the aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles such as e.g. 2-nonenenitrile; 2-undecenenitrile; 2 tridecenenitrile; 3,12-tridecadienenitrile; 3,7-dimethyl-2,6-octadienenitrile; 3,7-dimethyl-6 octenenitrile;

the esters of aliphatic carboxylic acids such as e.g. (E) and (Z)-3-hexenyl formate; ethyl acetoacetate; isoamyl acetate; hexyl acetate; 3,5,5-trimethylhexyl acetate; 3 methyl-2-butenyl acetate; (E)-2-hexenyl acetate; (E) and (Z)-3-hexenyl acetate; octyl acetate; 3-octyl acetate; 1-octen-3-yl acetate; ethyl butyrate; butyl butyrate; isoamyl butyrate; hexyl butyrate; (E) and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxy acetate; methyl-3,7-dimethyl-2,6-octadienoate; 4-methyl-2-pentyl crotonate;

the acyclic terpene alcohols such as e.g. geraniol; nerol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2 ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2 butenoates thereof;

the acyclic terpene aldehydes and ketones such as e.g. geranial; neral; citronellal; 7 hydroxy-3,7-dimethyloctanal; 7 methoxy-3,7-dimethyloctanal; 2,6,10-trimethyl-9 undecenal; geranyl acetone; as well as the dimethyl and diethylacetals of geranial, neral, 7-hydroxy-3,7-dimethyloctanal; the cyclic terpene alcohols such as e.g. menthol; isopulegol; alphaterpineol; terpine-4-ol; menthan-8-ol; menthan-1-ol; menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

the cyclic terpene aldehydes and ketones such as e.g. menthone; isomenthone; 8 mercaptomenthan-3-one; carvone; camphor; fenchone; alpha-ionone; beta-ionone; alpha-n-methylionone; beta-n-methylionone; alpha-isomethylionone; beta-isomethylionone; alphairone; alpha-damascone; beta-damascone; beta-damascenone; delta-damascone; gammadamascone; 1-(2,4,4-trimethyl-2-cyclohexen-1-yl)-2-buten-1-one; 1,3,4,6,7,8a-hexahydro-1,1,5,5-tetramethyl-2H-2,4a-methano¬inaphthalene-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methyl cedryl ketone);

the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha-3,3-trimethylcyclohexylmethanol; 1 (4-isopropylcyclohexyl)ethanol; 2-methyl-4-(2,2,3-trimethyl-3-cyclopent-1-yl)butanol; 2-methyl-4-(2,2,3 trimethyl-3-cyclopent-1-yl)-2-buten-1-ol; 2-ethyl-4-(2,2,3-trimethyl-3 cyclopent-1-yl)-2-buten-1-ol; 3-methyl-5-(2,2,3 trimethyl-3-cyclopent-1-yl)pentan-2 ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl) hexan-3-ol;

the cyclic and cycloaliphatic ethers such as e.g. cineol; cedryl methyl ether; cyclododecyl methyl ether; 1,1-dimethoxycyclododecane; (ethoxymethoxy)cyclo-dodecane; alphacedrene epoxide; 3a,6,6,9a-tetramethyl-dodecahydronaphtho[2,1-b]furan; 3a-ethyl-6,6,9a-trimethyldodecahydro-naphtho[2,1-b]furan; 1,5,9-trimethyl-13-oxabicyclo-[10.1.0]trideca-4,8-diene; rose oxide; 2-(2,4-dimethyl-3-cyclohexen-1-yl)-5-methyl-5-(1-methylpropyl)-1,3-dioxane;

the cyclic and macrocyclic ketones such as e.g. 4-tert-butylcyclohexanone; 2,2,5 trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2 cyclopenten-1-one; 3-methyl-2-pentyl-2-cyclopenten-1-one; 3-methyl-4-cyclopenta-decenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclo-hexadecen-1-one; 7-cyclohexadecen-1-one; (7/8)-cyclohexadecen-1-one; 9 cyclo-heptadecen-1-one; cyclopentadecanone; cyclohexadecanone; the cycloaliphatic aldehydes such as e.g. 2,4-dimethyl-3-cyclohexenecarbaldehyde; 2 methyl-4-(2,2,6-trimethylcyclohexen-1-yl)-2-butenal; 4-(4-hydroxy-4-methylpentyl)-3 cyclohexene carbaldehyde; 4-(4-methyl-3-penten-1-yl)-3-cyclohexenecarbaldehyde;

the cycloaliphatic ketones such as e.g. 1-(3,3-dimethyl-cyclohexyl)-4-penten-1-one; 2,2 dimethyl-1-(2,4-dimethyl-3-cyclohexen-1-yl)-1-propanone; 1-(5,5-dimethyl-1 cyclo-hexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclodo-decatrienyl ketone; tert-butyl (2,4-dimethyl-3-cyclohexen-1-yl) ketone;

the esters of cyclic alcohols such as e.g. 2-tert-butylcyclohexyl acetate; 4-tertbutylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6 indenyl propionate; 4,7-methano-3a,4,5,6,7,7a-hexahydro-5 or 6-indenyl isobutyrate; 4,7 methanooctahydro-5 or 6-indenyl acetate;

the esters of cycloaliphatic alcohols such as e.g. 1-cyclohexylethyl crotonate;

the esters of cycloaliphatic carboxylic acids such as e.g. allyl 3-cyclohexylpropionate; allyl cyclohexyloxyacetate; cis and trans-methyl dihydrojasmonate; cis and trans-methyl jasmonate; methyl 2-hexyl-3-oxocyclopentanecarboxylate; ethyl 2-ethyl-6,6 dimethyl-2-cyclohexenecarboxylate; ethyl 2,3,6,6-tetramethyl-2 cyclohexene-carboxylate; ethyl 2-methyl-1,3-dioxolane-2-acetate;

the araliphatic alcohols such as e.g. benzyl alcohol; 1-phenylethyl alcohol, 2 phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2 phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxy benzyl alcohol; 1-(4-isopropylphenyl)ethanol;

the esters of araliphatic alcohols and aliphatic carboxylic acids such as e.g. benzyl acetate;

benzyl propionate; benzyl isobutyrate; benzyl isovalerate; 2-phenylethyl acetate; 2-phenylethyl propionate; 2-phenylethyl isobutyrate; 2 phenylethyl isovalerate; 1 phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers such as e.g. 2-phenylethyl methyl ether; 2 phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m dioxine;

the aromatic and araliphatic aldehydes such as e.g. benzaldehyde; phenylacetaldehyde; 3-phenylpropanal; hydratropaaldehyde; 4-methylbenzaldehyde; 4 methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tertbutylphenyl)propanal; cinnamaldehyde; alpha-butylcinnamaldehyde; alphaamylcinnamaldehyde; alpha-hexylcinnamaldehyde; 3 methyl-5-phenylpentanal; 4-methoxybenzaldehyde; 4-hydroxy-3 methoxy-benzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as e.g. acetophenone; 4-methylacetophenone; 4-methoxyacetophenone; 4-tert-butyl-2,6-dimethylaceto-phenone; 4-phenyl-2-butanone; 4-(4-hydroxyphenyl)-2-butanone; 1-(2-naphthalenyl)-ethanone; 2-benzofuranylethanone; (3-methyl-2-benzofuranyl)ethanone; benzophenone; 1,1,2,3,3,6-hexamethyl-5-indanyl methyl ketone; 6-tert-butyl-1,1 dimethyl-4 indanyl methyl ketone; 1-[2,3-dihydro-1,1,2,6-tetramethyl-3-(1-methylethyl)-1H-5 indenyl]ethanone; 5',6',7',8'-tetrahydro-3',5',5',6',8',8'-hexamethyl-2-acetonaphthone;

the aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds such as e.g. 2,4,6-trinitro-1,3-dimethyl-5 tertbutylbenzene; 3,5-dinitro-2,6-dimethyl-4-tert-butylacetophenone; cinnamonitrile; 3 methyl-5-phenyl-2-pentenonitrile; 3-methyl-5-phenylpentanonitrile; methyl anthranilate; methyl-N methylanthranilate; Schiff bases of methyl anthranilate with 7 hydroxy-3,7-dimethyloctanal, 2-methyl-3-(4-tert-butylphenyl)propanal or 2,4 dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3 isopropyl-pyrazine; 2-isobutyl-3-methoxypyrazine;

the phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2 ethoxy-5-(1-propenyl)phenol; p-cresyl phenylacetate;

the heterocyclic compounds such as e.g. 2,5-dimethyl-4-hydroxy-2H-furan-3-one; 2 ethyl-4-hydroxy-5-methyl-2H-furan-3-one; 3-hydroxy-2-methyl-4H-pyran-4-one; 2 ethyl-3-hydroxy-4H-pyran-4-one;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis and trans-11-pentadecen-1,15-olide; cis and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

In a preferred embodiment, the at least one non-aroma chemical carrier (ii) is selected from the group consisting of surfactants, oil components, anti-oxidants, deodorant-active agents and solvents.

In the context of the presently claimed invention, a "solvent" serves for the dilution of the compound of formula (I) to be used according to the invention and/or any further component of the composition without having its own aroma.

The amount of solvent(s) is selected depending on the composition.

In yet another preferred embodiment, the solvent is selected from the group consisting of ethanol, isopropanol, diethylene glycol monoethyl ether, glycerol, propylene glycol, 1,2-butylene glycol, dipropylene glycol, triethyl citrate and isopropyl myristate.

In yet another preferred embodiment, the solvent is present in the composition in an amount of 0.01 wt. % to 99.0 wt. %, more preferably in an amount of 0.05 wt. % to 95.0 wt. %, yet more preferably in an amount of 0.1 wt. % to 80.0 wt. %, most preferably 0.1 wt. % to 70.0 wt. %, particularly in an amount of 0.1 wt. % to 60.0 wt. %, based on the total weight of the composition.

In yet another preferred embodiment of the invention, the composition comprises 0.05 wt. % to 10 wt. %, more preferably 0.1 wt. % to 5 wt. %, yet more preferably 0.2 wt. % to 3 wt. % so-vent(s), based on the total weight of the composition. In yet another preferred embodiment of the invention, the composition comprises 20 wt. % to 70 wt. %, more preferably 25 wt. % to 50 wt. % of solvent(s), based on the total weight of the composition.

One embodiment of the invention is directed to a composition comprising the compound of formula (I) and at least one oil component.

In a preferred embodiment, the oil components are present in an amount of 0.1 to 80 wt. %, more preferably 0.5 to 70 wt. %, yet more preferably 1 to 60 wt. %, even more preferably 1 to 50 wt. %, particularly 1 to 40 wt. %, more particularly 5 to 25 wt. % and specifically 5 to 15 wt. %, based on the total weight of the composition.

The oil components may be selected, for example, from Guerbet alcohols based on fatty alcohols containing 6 to 18, preferably 8 to 10, carbon atoms and other additional esters, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of C18-C38 alkylhydroxycarboxylic acids with linear or branched C6-C22 fatty alcohols, more especially dioctyl malate, esters of linear and/or branched fatty acids with polyhydric alcohols (for example propylene glycol, dimer diol or trimer triol), triglycerides based on C6-C10 fatty acids, liquid mono-, di- and triglyceride mixtures based on C6-C18 fatty acids, esters of C6-C22 fatty alcohols and/or Guerbet alcohols with aromatic carboxylic acids, more particularly benzoic acid, esters of dicarboxylic acids with polyols containing 2 to 10 carbon atoms and 2 to 6 hydroxyl groups, vegetable oils, branched primary alcohols, substituted cyclohexanes, linear and branched C6-C22 fatty alcohol carbonates such as, for example, dicaprylyl carbonate (Cetiol® CC), Guerbet carbonates based on fatty alcohols containing 6 to 18, preferably 8 to 10, carbon atoms, esters of benzoic acid with linear and/or branched C6 to C22 alcohols (for example Finsov® TN), linear or branched, symmetrical or nonsymmetrical dialkyl ethers containing 6 to 22 carbon atoms per alkyl group such as, for example, dicaprylyl ether (Cetiol® OE), ring opening products of epoxidized fatty acid esters with polyols and hydrocarbons or mixtures thereof.

It is to be understood that anti-oxidants are able to inhibit or prevent the undesired changes in the compositions to be protected caused by oxygen effects and other oxidative processes. The effect of the anti-oxidants consists in most cases in them acting as free-radical scavengers for the free radicals which arise during autoxidation.

In a preferred embodiment, the anti-oxidant is selected from the group consisting of
- amino acids (for example glycine, alanine, arginine, serine, threonine, histidine, tyrosine, tryptophan) and derivatives thereof,
- imidazoles (e.g. urocanic acid) and derivatives thereof,
- peptides, such as D,L-carnosine, D-carnosine, L-carnosine (=β-Alanyl-L-histidin) and derivatives thereof
- carotenoids, carotenes (e.g. alpha-carotene, beta-carotene, lycopene, lutein) or derivatives thereof,
- chlorogenic acid and derivatives thereof,
- lipoic acid and derivatives thereof (for example dihydrolipoic acid),
- auro-thioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, gamma-linoleyl, cholesteryl and glyceryl esters thereof) and salts thereof,
- dilauryl thiodipropionate, distearyl thiodipropionate, thiodipropionic acid and derivatives thereof (esters, ethers, peptides, lipids, nucleotides, nucleosides and salts),
- sulfoximine compounds (for example buthionine sulfoximines, homocysteine sulfoximine, buthionine sulfones, penta-, hexa-, heptathionine sulfoximine)
- (metal) chelating agents (e.g. alpha-hydroxy fatty acids, palmitic acid, phytic acid, lactoferrin),
- alpha-hydroxy acids (for example citric acid, lactic acid, malic acid),
- humic acid, bile acid, bile extracts, bilirubin, biliverdin, boldin (=alkaloid from the plant *Peumus boldus*, boldo extract,
- EDTA, EGTA and derivatives thereof,
- unsaturated fatty acids and derivatives thereof (e.g. gamma-linolenic acid, linoleic acid, oleic acid),
- folic acid and derivatives thereof,
- ubiquinone and ubiquinol and derivatives thereof,
- vitamin C and derivatives (for example ascorbyl palmitate, Mg ascorbyl phosphate, ascorbyl acetate),
- tocopherols and derivatives (for example vitamin E acetate),
- vitamin A and derivatives (for example vitamin A palmitate),
- coniferyl benzoate of gum benzoin, rutic acid and derivatives thereof, alphaglycosylrutin, ferulic acid, furfurylideneglucitol,
- butylhydroxytoluene (BHT), butylhydroxyanisole (BHA)
- nordihydroguaiacic acid, nordihydroguaiaretic acid, trihydroxybutyrophenone, uric acid and derivatives thereof, mannose and derivatives thereof,
- superoxide dismutase
- zinc and derivatives thereof (for example ZnO, ZnSO4),
- selenium and derivatives thereof (for example selenomethionine) and
- stilbenes and derivatives thereof (e.g. stilbene oxide, trans-stilbene oxide)

In a preferred embodiment, the anti-oxidant is selected from the group consisting of pentaerythrityl, tetra-di-t-butyl-hydroxyhydrocinnamate, nordihydroguaiaretic acid, ferulic acid, resveratrol, propyl gallate, butylhydroxytoluene (BHT), butylhydroxyanisole (BHA), ascorbyl palmitate and tocopherol.

In yet another preferred embodiment, the compositions according to the presently claimed invention can comprise the anti-oxidant in an amount of 0.001 to 25 wt.-%, preferably 0.005 to 10 wt.-%, more preferably 0.01 to 8 wt.-%, yet more preferably 0.025 to 7 wt.-%, even more preferably 0.05 to 5 wt.-%, based on the total weight of the composition.

Deodorizing compositions (deodorants and antiperspirants) counteract, mask or eliminate body odors. Body odors are formed through the action of skin bacteria on apocrine perspiration which results in the formation of unpleasant-smelling degradation products.

One embodiment of the invention is therefore directed to a composition comprising the compound of formula (I) and at least one deodorant-active agent. In a preferred embodiment, the deodorant-active agent is selected from the groups consisting of anti-perspirants, esterase inhibitors and anti-bacterial agents.

Suitable antiperspirant is selected from the group consisting of salts of aluminum, zirconium or zinc. Examples are aluminum chloride, aluminum chlorohydrate, aluminum dichlorohydrate, aluminum sesquichlorohydrate and complex compounds thereof, for example with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, for example with amino acids, such as glycine. Aluminum chlorohydrate, aluminum zirconium tetrachlorohydrate, aluminum zirconium pentachlorohydrate and complex compounds thereof are preferably used.

In a preferred embodiment, the anti-perspirant is selected from the group consisting of aluminum chloride, aluminum chlorohydrate, aluminum dichlorohydrate, aluminum sesquichlorohydrate, aluminum hydroxyallantoinate, aluminum chloride tartrate, aluminum zirconium trichlorohydrate, aluminum zirconium tetrachlorohydrate and aluminum zirconium pentachlorohydrate.

Where perspiration is present in the underarm region, extracellular enzymes-esterases, mainly proteases and/or lipases are formed by bacteria and split the esters present in the perspiration, releasing odors in the process. Suitable esterase inhibitors are for example trialkyl citrates, such as trimethyl citrate, tripropyl citrate, triisopropyl citrate, tributyl citrate and, in particular, triethyl citrate. Esterase inhibitors inhibit enzyme activity and thus reduce odor formation. The free acid is probably released by the cleavage of the citric acid ester and reduces the pH value of the skin to such an extent that the enzymes are inactivated by acylation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

In a preferred embodiment, the esterase inhibitor is selected from the group consisting of trimethyl citrate, tripropyl citrate, triisopropyl citrate, tributyl citrate triethyl citrate, lanosterol, cholesterol, campesterol, stigmasterol, sitosterol sulfate, sitosterol phosphate, glutaric acid, glutaric acid monoethyl ester, glutaric acid diethyl ester, adipic acid, adipic acid monoethyl ester, adipic acid diethyl ester, malonic acid, malonic acid diethyl ester, citric acid, malic acid, tartaric acid, tartaric acid diethyl ester and zinc glycinate.

The compositions according to the presently claimed invention comprises the esterase inhibitor in the range of 0.01 to 20 wt.-%, preferably 0.1 to 10 wt.-% and more particularly 0.5 to 5 wt.-%, based on the total weight of the composition.

The term "anti-bacterial agents" as used herein encompasses substances which have bactericidal and/or bacteriostatic properties. Typically these substances act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

In a preferred embodiment, the antibacterial agent is selected from the group consisting of chitosan, phenoxyethanol, 5-chloro-2-(2,4-dichlorophenoxy)-phenol, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylenebis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), phenoxyethanol, glycerol monocaprate, glycerol monocaprylate, glycerol monolaurate (GML), diglycerol monocaprate (DMC), salicylic acid-N-alkylamides.

The composition according to the presently claimed invention comprises the antibacterial agent in the range of 0.01 to 5 wt. % and preferably 0.1 to 2 wt.-%, based on the total weight of the composition.

In a preferred embodiment, the composition preferably comprises a surfactant. Due to the characteristic fragrance property of the compound of formula (I) and its substantivity, tenacity as well as stability, it can especially be used to provide an odor, preferably a fragrance impression or aroma impression to surfactant-containing compositions such as, for example, cleaners (in particular laundry care products and all-purpose cleaners). It can preferably be used to impart a long-lasting a flowery and/or a marine and/or a green and/or a sweet note and/or a rubbery note and/or a nutty note and/or a woody note and/or a dusty note and/or a rooty note and/or a lemon note odiferous impression to a surfactant comprising composition.

In a preferred embodiment, the surfactant is selected from the group consisting of anionic, non-ionic, cationic, amphoteric and zwitterionic surfactants. In yet another preferred embodiment, the surfactant is an anionic surfactant.

The compositions according to the presently claimed invention can thus preferably comprise at least one surfactant. The surfactant(s) may be selected from anionic, non-ionic, cationic and/or amphoteric or zwitterionic surfactants. Surfactant-containing compositions, such as for example shower gels, foam baths, shampoos, etc., preferably contain at least one anionic surfactant.

The compositions according to the invention usually contain the surfactant(s), in the aggregate, in an amount of 0 to 40 wt. %, preferably 0 to 20 wt. %, more preferably 0.1 to 15 wt. %, and particularly 0.1 to 10 wt. %, based on the total weight of the composition. Typical examples of non-ionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolysates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Zwitterionic surfactants are surface-active compounds which contain at least one quaternary ammonium group and at least one COO(–) or SO3(–) group in the molecule. Particularly suitable zwitterionic surfactants are the so-called betaines, such as the N-alkyl-N,N-dimethyl ammonium glycinates, for example, cocoalkyl dimethyl ammonium glycinate, N-acylaminopropyl-N,N-dimethyl ammonium glycinates, for example, cocoacylaminopropyl dimethyl ammonium glycinate, and 2-alkyl-3-carboxymethyl-3-hydroxyethyl imidazolines, containing 8 to 18 carbon atoms in the alkyl or acyl group, and cocoacylaminoethyl hydroxyethyl carboxymethyl glycinate. The fatty acid amide derivative known under the CTFA name of Cocamidopropyl Betaine is particularly preferred.

Ampholytic surfactants are also suitable, particularly as co-surfactants. Ampholytic surfactants are surface-active compounds which, in addition to a C8 to C18 alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkylaminobutyric acids, Nalkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalk-ylaminopropionate, cocoacylaminoethyl aminopropionate and acyl sarcosine.

Anionic surfactants are characterized by a water-solubilizing anionic group such as, for example, a carboxylate, sulfate, sulfonate or phosphate group and a lipophilic group. Dermatologically safe anionic surfactants are known to the practitioner in large numbers from relevant textbooks and are commercially available. They are, in particular, alkyl sulfates in the form of their alkali metal, ammonium or alkanolammonium salts, alkylether sulfates, alkylether carboxylates, acyl isethionates, acyl sarcosinates, acyl taurines containing linear C12-C18 alkyl or acyl groups and sulfosuccinates and acyl glutamates in the form of their alkali metal or ammonium salts.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example, cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as, for example, the dialkyl ammonium methosulfates and methyl hydroxyalkyl dialkoyloxyalkyl ammonium methosulfates marketed under the name of Stepantexe and the corresponding products of the Dehyquart® series, may be used as cationic surfactants. "Esterquats" are generally understood to be quaternized fatty acid triethanolamine ester salts. They can provide the compositions with particular softness. They are known substances which are prepared by the relevant methods of organic chemistry. Other cationic surfactants suitable for use in accordance with the invention are the quaternized protein hydrolysates.

One embodiment of the presently claimed invention is directed to a composition which is selected from the group consisting of perfume compositions, body care compositions, hygiene articles, cleaning compositions, textile detergent compositions, compositions for scent dispensers, foods, food supplements, pharmaceutical compositions and crop protection compositions.

Said composition is preferably an aroma chemical composition, more preferably a fragrance composition.

Suitable compositions are for example perfume compositions, body care compositions (including cosmetic compositions and products for oral and dental hygiene), hygiene articles, cleaning compositions (including dishwashing compositions), textile detergent compositions, compositions for scent dispensers, foods, food supplements, pharmaceutical compositions and crop protection compositions.

Perfume compositions can be selected from fine fragrances, air fresheners in liquid form, gel-like form or a form applied to a solid carrier, aerosol sprays, scented cleaners, perfume candles and oils, such as lamp oils or oils for massage.

Examples for fine fragrances are perfume extracts, Eau de Parfums, Eau de Toilettes, Eau de Colognes, Eau de Solide and Extrait Parfum.

Body care compositions include cosmetic compositions and products for oral and dental hygiene, and can be selected from after-shaves, pre-shave products, splash colognes, solid and liquid soaps, shower gels, shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, after-sun creams and lotions, hand creams and lotions, foot creams and lotions, hair removal creams and lotions, after-shave creams and lotions, tanning creams and lotions, hair care products such as e.g. hairsprays, hair gels, setting hair lotions, hair conditioners, hair shampoo, permanent and semi-permanent hair colorants, hair shaping compositions such as cold waves and hair smoothing compositions, hair tonics, hair creams and hair lotions, deodorants and antiperspirants such as e.g. underarm sprays, roll-ons, deodorant sticks and deodorant creams, products of decorative cosmetics such as e.g. eye-liners, eyeshadows, nail varnishes, make-ups, lipsticks and mascara, and products for oral and dental hygiene, such as toothpaste, dental floss, mouth wash, breath fresheners, dental foam, dental gels and dental strips.

Hygiene articles can be selected from joss sticks, insecticides, repellents, propellants, rust removers, perfumed freshening wipes, armpit pads, baby diapers, sanitary towels, toilet paper, cosmetic wipes, pocket tissues, dishwasher and deodorizer.

Cleaning compositions, such as e.g. cleaners for solid surfaces, can be selected from perfumed acidic, alkaline and neutral cleaners, such as e.g. floor cleaners, window cleaners, dishwashing compositions both for handwashing and machine washing use, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, limescale removers, grill and oven cleaners, algae and moss removers, mold removers, facade cleaners.

Textile detergent compositions can be selected from liquid detergents, powder detergents, laundry pretreatments such as bleaches, soaking agents and stain removers, fabric softeners, washing soaps, washing tablets.

Food means a raw, cooked, or processed edible substance, ice, beverage or ingredient used or intended for use in whole or in part for human consumption, or chewing gum, gummies, jellies, and confectionaries.

A food supplement is a product intended for ingestion that contains a dietary ingredient intended to add further nutritional value to the diet. A dietary ingredient may be one, or any combination, of the following substances: a vitamin, a mineral, an herb or other botanical, an amino acid, a dietary substance for use by people to supplement the diet by increasing the total dietary intake, a concentrate, metabolite, constituent, or extract. Food supplements may be found in many forms such as tablets, capsules, soft gels, gel caps, liquids, or powders.

Pharmaceutical compositions comprise compositions which are intended for use in the diagnosis, cure, mitigation, treatment, or prevention of disease as well as articles (other than food) intended to affect the structure or any function of the body of man or other animals.

Crop protection compositions comprise compositions which are intended for the managing of plant diseases, weeds and other pests (both vertebrate and invertebrate) that damage agricultural crops and forestry.

In a preferred embodiment, the composition further comprises at least one auxiliary agent selected from the group consisting of preservatives, abrasives, anti-acne agents, agents to combat skin aging, anti-cellulite agents, antidandruff agents, anti-inflammatory agents, irritation-preventing agents, irritation-alleviating agents, astringents, sweat-inhibiting agents, antiseptics, anti-statics, binders, buffers, carrier materials, chelating agents, cell stimulants, care agents, hair removal agents, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, opacifiers, plasticizers, covering agents, polish, shine agents, polymers, powders, proteins, refatting agents, exfoliating agents, silicones, skin-calming agents, skin-cleansing agents, skin care agents, skin-healing agents, skin lightening agents, skin-protective agents, skin-softening agents, cooling agents, skin-cooling agents, warming agents, skin-warming agents, stabilizers, UV-absorbent agents, UV filters, fabric softeners, suspending agents, skin-tanning agents, thickeners, vitamins, waxes, fats, phospholipids, saturated fatty acids, mono- or polyunsaturated fatty acids, α-hydroxy acids, polyhydroxy fatty acids, liquefiers, dyes, color-protection agents, pigments, anti-corrosives, polyols, electrolytes and silicone derivatives.

Mixture

An embodiment of the present invention is directed to a mixture comprising compound of formula (I),

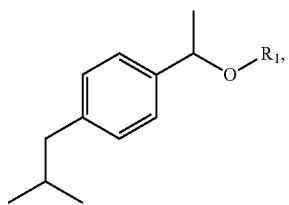

formula (I)

wherein
R₁ is selected from the group consisting of linear or branched, unsubstituted —C₁-O₅ alkyl and unsubstituted —C₃-C₅ cycloalkyl;
or its salt or stereoisomer thereof; and
4-methyl-2-(2-methylpropyl)oxan-4-ol.

In a further embodiment of the present invention, the mixture comprises compound of formula (I) wherein R₁ is selected from the group consisting of —CH₃, —CH₂CH₃, —CH₂CH₂CH₃, —CH(CH₃)₂, —CH(CH₃)(C₂H₅), —CH₂CH(CH₃)₂, —CH₂CH₂CH₂CH₃, —CH(CH₃)₂, —CH₂CH(CH₃)₂, —CH(CH₃)CH₂CH₃ and cyclopropyl.

In an embodiment of the present invention, the mixtures are according to the below table M

TABLE M:

| Mixture | R₁ of formula (I) | |
|---|---|---|
| 1 | —CH₃ | 4-methyl-2-(2-methylpropyl)oxan-4-ol |
| 2 | —CH₂CH₃ | 4-methyl-2-(2-methylpropyl)oxan-4-ol |
| 3 | —CH₂CH₂CH₃ | 4-methyl-2-(2-methylpropyl)oxan-4-ol |
| 4 | —CH(CH₃)₂ | 4-methyl-2-(2-methylpropyl)oxan-4-ol |
| 5 | —CH(CH₃)(C₂H₅) | 4-methyl-2-(2-methylpropyl)oxan-4-ol |
| 6 | —CH(CH₃)₂ | 4-methyl-2-(2-methylpropyl)oxan-4-ol |
| 7 | —CH₂CH₂CH₂CH₃ | 4-methyl-2-(2-methylpropyl)oxan-4-ol |
| 8 | —CH(CH₃)₂ | 4-methyl-2-(2-methylpropyl)oxan-4-ol |
| 9 | —CH₂CH(CH₃)₂ | 4-methyl-2-(2-methylpropyl)oxan-4-ol |
| 10 | —CH(CH₃)CH₂CH₃ | 4-methyl-2-(2-methylpropyl)oxan-4-ol |
| 11 | cyclopropyl | 4-methyl-2-(2-methylpropyl)oxan-4-ol |

In another embodiment of the present invention, the mixture comprises compound of formula (I), wherein R₁ is preferably —CH₂CH₃, —CH(CH₃)₂.

In a further embodiment of the present invention, the mixture according to the above embodiments is used to impart an aroma impression to a composition.

In a further embodiment of the present invention, the ratio of the compound of formula (I) as described above and 4-methyl-2-(2-methylpropyl)oxan-4-ol is in the range of ≥1:2 to ≤1:25, preferably ≥1:3 to ≤1:20; more preferably ≥1:4 to ≤1:20.

In a further embodiment of the present invention, the ratio of the compound of formula (I) as described above and 4-methyl-2-(2-methylpropyl)oxan-4-ol is 1:4, 1:5, 1:6, 1:7, 1:8, 1:9, 1:10, 1:11, 1:12, 1:13, 1:14, 1:5, 1:16. 1:17, 1:18, 1:19, 1:20.

In yet another embodiment of the present invention, the mixture according to the above embodiments, provides aroma impression, which is reminiscent of a floral, muguet, powdery note.

In another embodiment of the present invention, the composition comprising,
(i) the mixture according to any of embodiments above and
(ii) at least one aroma chemical, or
(iii) at least one non-aroma chemical carrier, or
(iv) both of (ii) and (iii).

Compound

One embodiment of the presently claimed invention is directed to a compound of formula (I'),

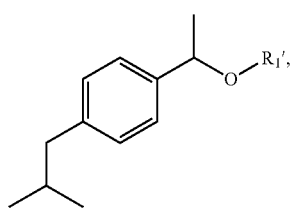

formula (I')

wherein
R₁' is selected from the group consisting of linear or branched —CH₂CH₂CH₃, —CH(CH₃)(C₂H₅), —CH₂CH(CH₃)₂, —CH(CH₃)CH₂CH₃ and —CH₂CH₂CH₂CH₃;
or its salt or stereoisomer thereof.

In a preferred embodiment, R₁' is —CH₂CH₂CH₃. In yet another embodiment, R₁' is —CH(CH₃)(C₂H₅). In a further preferred embodiment, R₁' is —CH(CH₃)CH₂CH₃. In yet another preferred embodiment, R₁' is —CH₂CH(CH₃)₂. In yet another embodiment, R₁' is —CH₂CH₂CH₂CH₃.

Embodiments

In the following, there is provided a list of embodiments to further illustrate the present disclosure without intending to limit the disclosure to the specific embodiments listed below.

1. Use of a compound of formula (I),

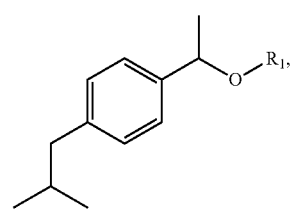

formula (I)

wherein
R₁ is selected from the group consisting of linear or branched, unsubstituted —C₁-C₅ alkyl and unsubstituted —C₃-C₅ cycloalkyl;
or its salt or stereoisomer thereof,
to impart an aroma impression to a composition.

2. Method of imparting an aroma impression to a composition comprising
at least the step of adding a compound of formula (I),

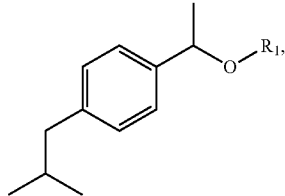

formula (I)

wherein
R₁ is selected from the group consisting of linear or branched, unsubstituted —C₁-C₅ alkyl and unsubstituted —C₃-C₅ cycloalkyl;
or its salt or stereoisomer thereof,
to a composition.

3. The use or method according to any of the preceding embodiments, wherein R₁ is selected from the group consisting of —CH₃, —CH₂CH₃, —CH₂CH₂CH₃, —CH(CH₃)₂, —CH(CH₃)(C₂H₅), —CH₂CH(CH₃)₂, —CH₂CH₂CH₂CH₃ and cyclopropyl.

4. The use or method according to any of the preceding embodiments, wherein the composition selected from perfume compositions, body care compositions, hygiene articles, cleaning compositions, textile detergent compositions, compositions for scent dispensers, foods, food supplements, pharmaceutical compositions and crop protection compositions.

5. The use or method according to any of the preceding embodiments, wherein the impression is selected from a group consisting of a flowery note, a marine note, a sweet note, a rubbery note, a nutty note, a woody note, a dusty note, a rooty note, a lemon note and a green note.

6. The use or method according to any of the preceding embodiments, wherein the compound of formula (I) or its salts or stereoisomer is present in an amount in the range of ≥0.01 wt. % to ≤70.0 wt. %, based on the total weight of the composition.

7. A composition comprising a at least one compound of the formula (I),

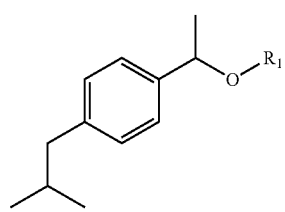

formula (I)

wherein
R₁ is selected from the group consisting of linear or branched, unsubstituted —C₂-C₅ alkyl and unsubstituted —C₃-C₅ cycloalkyl;
or its salt or stereoisomer thereof and
(i) at least one aroma chemical, or
(ii) at least one non-aroma chemical carrier, or
(iii) both of (i) and (ii).

8. The composition according to embodiment 7, wherein R₁ is selected from the group consisting of —CH₂CH₃, —CH₂CH₂CH₃, —CH(CH₃)₂, —CH(CH₃)(C₂H₅), —CH₂CH(CH₃)₂, —CH₂CH₂CH₂CH₃, cyclopropyl and cyclobutyl.

9. The composition according to embodiment 7 or 8, wherein the at least one aroma chemical (i) is selected from the group consisting of geranyl acetate, alphahexylcinnamaldehyde, 2-phenoxyethyl isobutyrate, dihydromyrcenol, methyl dihydrojasmonate, 4,6,6,7,8,8-hexamethyl-1,3,4,6,7,8-hexahydrocyclopenta[g]benzopyran, tetrahydrolinalool, ethyllinalool, benzyl salicylate, 2-methyl-3-(4-tertbutylphenyl)propanal, cinnamyl alcohol, 4,7-methano-3a,4,5,6,7,7a-hexahydro-5-indenyl acetate and/or 4,7-methano-3a,4,5,6,7,7a-hexahydro-6-indenyl acetate, citronellol, citronellyl acetate, tetrahydrogeraniol, vanillin, linalyl acetate, styrolyl acetate, octahydro-2,3,8,8-tetramethyl-2-acetonaphthone and/or 2-acetyl-1,2,3,4,6,7,8-octahydro-2,3,8,8-tetramethylnaphthalene, hexyl salicylate, 4-tert-butylcyclohexyl acetate, 2-tert-butylcyclohexyl acetate, alpha-ionone, n-alpha-methylionone, alphaisomethylionone, coumarin, terpinyl acetate, 2-phenylethyl alcohol, 4-(4-hydroxy-4-methylpentyl)-3-cyclohexene-carboxaldehyde, alpha-amylcinnamaldehyde, ethylene brassylate, (E)- and/or (Z)-3-methylcyclopentadec-5-enone, 15-pentadec-11-enolide and/or 15-pentadec-12-enolide, 15-cyclopentadecanolide, 1-(5,6,7,8-tetrahydro-3,5,5,6,8,8-hexamethyl-2-naphthalenyl)ethanone, 2-isobutyl-4-methyltetrahydro-2H-pyran-4-ol, 2-ethyl-4-(2,2,3-trimethyl-3-cyclopenten-1-yl)-2-buten-1-ol, cis-3-hexenyl acetate, trans-3-hexenyl acetate, trans-2/cis-6-nonadienol, 2,4-dimethyl-3-cyclohexenecarboxaldehyde, 2,4,4,7-tetramethyloct-6-en-3-one, 2,6-dimethyl-5-hepten-1-al, borneol, 3-(3-isopropylphenyl)butanal, 2-methyl-3-(3,4-methylenedioxyphenyl)propanal, 3-(4-ethylphenyl)-2,2-dimethylpropanal, 7-methyl-2H-1,5-benzodioxepin-3(4H)-one, 3,3,5-trimethylcyclohexyl acetate, 2,5,5-trimethyl-1,2,3,4,4a,5,6,7-octahydronaphthalen-2-ol, 3-(4-tert-butylphenyl)-propanal, ethyl 2-methylpentanoate, ethoxymethoxycyclododecane, 2,4-dimethyl-4,4a,5,9b-tetrahydroindeno[1,2-d][1,3]dioxine, (2-tert-butylcyclohexyl) acetate and 3-[5,5,6-trimethyl bicyclo [2.2.1]hept-2-yl]cyclohexan-1-ol.

10. The composition according to the embodiment 7 or 8, wherein the at least one aroma chemical (i) is selected from the group consisting of methyl benzoate, benzyl acetate, geranyl acetate, 2-isobutyl-4-methyltetrahydro-2H-pyran-4-ol, linalool, 2-isobutyl-4-methyltetrahydro-2H-pyran-4-ol and methyl benzoate.

11. The composition according to the embodiment 7 or 8, wherein the at least one aroma chemical (i) is selected from the group consisting of ethylvanillin, vanillin, 2,5-dimethyl-4-hydroxy-2H-furan-3-one (furaneol) or 3-hydroxy-2-methyl-4H-pyran-4-one (maltol).

12. The composition according to any one of the embodiments 8 to 11, wherein the at least one non-aroma chemical carrier (ii) is selected from the group consisting of surfactants, oil components, anti-oxidants, deodorant-active agents and solvents.

13. The composition according to the embodiment 12, wherein the solvent is selected from the group consisting of ethanol, isopropanol, diethylene glycol monoethyl ether, glycerol, propylene glycol, 1,2-butylene glycol, dipropylene glycol, triethyl citrate and isopropyl myristate.

14. The composition according to embodiment 12 or 13, wherein the solvent is present in the composition in an amount of 0.01 wt. % to 99.0 wt. % based on the total weight of the composition.
15. The composition according to the embodiment 12, wherein the at least one deodorant-active agent is selected from the groups consisting of anti-perspirants, esterase inhibitors and antibacterial agents.
16. The composition according to the embodiment 15, wherein the anti-perspirant is selected from selected from the group consisting of aluminum chloride, aluminum chlorohydrate, aluminum dichlorohydrate, aluminum sesquichlorohydrate, aluminum hydroxyallantoinate, aluminum chloride tartrate, aluminum zirconium trichlorohydrate, aluminum zirconium tetrachlorohydrate and aluminum zirconium pentachlorohydrate.
17. The composition according to the embodiment 15, wherein the esterase inhibitor is selected from the group consisting of trimethyl citrate, tripropyl citrate, triisopropyl citrate, tributyl citrate triethyl citrate, lanosterol, cholesterol, campesterol, stigmasterol, sitosterol sulfate, sitosterol phosphate, glutaric acid, glutaric acid monoethyl ester, glutaric acid diethyl ester, adipic acid, adipic acid monoethyl ester, adipic acid diethyl ester, malonic acid, malonic acid diethyl ester, citric acid, malic acid, tartaric acid, tartaric acid diethyl ester and zinc glycinate.
18. The composition according to the embodiment 15, wherein the antibacterial agent is selected from the group consisting of chitosan, phenoxyethanol, 5-Chloro-2-(2,4-dichlorophenoxy)-phenol, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), phenoxyethanol, glycerol monocaprate, glycerol monocaprylate, glycerol monolaurate (GML), diglycerol monocaprate (DMC), salicylic acid-N-alkylamides.
19. The composition according to the embodiment 12, wherein the at least one surfactant is selected from the group consisting of anionic, non-ionic, cationic, amphoteric and zwitterionic surfactants.
20. The composition according to any one of the embodiments 12 or 19, wherein the at least one surfactant is an anionic surfactant.
21. The composition according to the embodiment 12, wherein the at least one antioxidant is selected from the group consisting of pentaerythrityl, tetra-di-t-butyl hydroxyhydrocinnamate, nordihydroguaiaretic acid, ferulic acid, resveratrol, propyl gallate, butylhydroxytoluene (BHT), butylhydroxyanisole (BHA), ascorbyl palmitate and tocopherol.
22. The composition according to any of the preceding embodiments 7 to 21, wherein the composition is selected from the group consisting of perfume compositions, body care compositions, hygiene articles, cleaning compositions, textile detergent compositions, compositions for scent dispensers, foods, food supplements, pharmaceutical compositions and crop protection compositions.
23. The composition according to any one of the preceding embodiments 7 to 22, wherein the composition further comprises at least one auxiliary agent selected from the group consisting of preservatives, abrasives, anti-acne agents, agents to combat skin aging, anti-cellulite agents, antidandruff agents, anti-inflammatory agents, irritation-preventing agents, irritation-alleviating agents, astringents, sweat-inhibiting agents, antiseptics, anti-statics, binders, buffers, carrier materials, chelating agents, cell stimulants, care agents, hair removal agents, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, opacifiers, plasticizers, covering agents, polish, shine agents, polymers, powders, proteins, refatting agents, exfoliating agents, silicones, skin-calming agents, skin-cleansing agents, skin care agents, skin-healing agents, skin lightening agents, skin-protective agents, skin-softening agents, cooling agents, skin-cooling agents, warming agents, skin-warming agents, stabilizers, UV-absorbent agents, UV filters, fabric softeners, suspending agents, skin-tanning agents, thickeners, vitamins, waxes, fats, phospholipids, saturated fatty acids, mono- or polyunsaturated fatty acids, α-hydroxy acids, polyhydroxy fatty acids, liquefiers, dyes, color-protection agents, pigments, anti-corrosives, polyols, electrolytes and silicone derivatives.
24. A mixture comprising compound of formula (I),

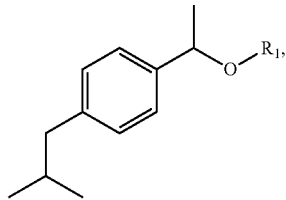

formula (I)

wherein $R_1$ is selected from the group consisting of linear or branched, unsubstituted —$C_1$-$C_5$ alkyl and unsubstituted —$C_3$-$C_5$ cycloalkyl;

or its salt or stereoisomer thereof; and 4-methyl-2-(2-methylpropyl)oxan-4-ol.
25. The mixture according to embodiment 24, wherein $R_1$ is selected from the group consisting of —$CH_3$, —$CH_2CH_3$, —$CH_2CH_2CH_3$, —$CH(CH_3)_2$, —$CH(CH_3)(C_2H_5)$, —$CH_2CH(CH_3)_2$, —$CH_2CH_2CH_2CH_3$, —$CH(CH_3)_2$, —$CH_2CH(CH_3)_2$, —$CH(CH_3)CH_2CH_3$ and cyclopropyl.
26. The mixture according to embodiment 24 or 25, wherein $R_1$ is selected from the group consisting of $CH_2CH_3$, —$CH(CH_3)_2$.
27. Use of the mixture according to any of the embodiments 24 to 26, to impart an aroma impression to a composition.

28. A composition comprising,
(i) the mixture according to any of the embodiment 24 to 26, and
(ii) at least one aroma chemical, or
(iii) at least one non-aroma chemical carrier, or
(iv) both of (ii) and (iii).

29. A compound of formula (I'),

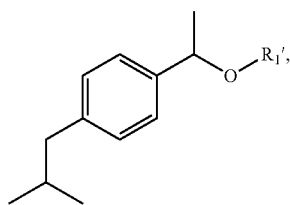

formula (I')

wherein
R₁' is selected from the group consisting of linear or branched —CH₂CH₂CH₃, —CH(CH₃)(C₂H₅), —CH₂CH(CH₃)₂, —CH(CH₃)CH₂CH₃ and —CH₂CH₂CH₂CH₃;
or its salt or stereoisomer thereof.

While the presently claimed invention has been described in terms of its specific embodiments, certain modifications and equivalents will be apparent to those skilled in the art and are intended to be included within the scope of the presently claimed invention.

EXAMPLES

The presently claimed invention is illustrated in detail by non-restrictive working examples which follow. More particularly, the test methods specified hereinafter are part of the general disclosure of the application and are not restricted to the specific working examples.

Analytical method: The characterization is done by $^{13}$C-NMR. The $^{13}$C-NMR spectra were measured on a Bruker DPX-500 spectrometer

1. Preparation of 1-(1-ethoxyethyl)-4-isobutylbenzene

Dry ethanol (60.47 g, 1.31 mol, 5 eq.) and sulfuric acid (96%, 3.22 g, 0.032 mol, 0.12 eq.) were mixed. Dry 1-(4-isobutylphenyl)ethanol (93.6 GC-a %, 50 g, 0.263 mol, 1 eq.) was added dropwise over 15 minutes. After complete addition, the mixture was brought to reflux (68° C.). After 7 h at reflux, the reaction mixture was cooled to room temperature and 100 mL ethylacetate and subsequently 50 mL of saturated NaHCO₃-solution were added. The mixture was stirred for 5 min and then, the phases were separated. The organic phase was dried over Na₂SO₄ and filtered. Then, the solvent was removed under reduced pressure to give 51.9 g of the desired crude product in a purity of 89 GC-a % (2 GC-a % not converted starting material; 85% yield (not based on rec. starting material)). The crude product was purified by fractional distillation (sump temperature 87-112° C., pressure 1.8-2.3 mbar). Fractions 2, 3 and 4 were united which contained the desired product in 96.6 GC-a % purity (and 0.8 GC-a % of starting material).

13C-NMR (125 MHz, CDCl₃): δ=140.7, 141.4, 129.1, 125.9, 77.6, 63.8, 45.2, 30.3, 24.2, 22.4, 15.4 ppm.

2. Preparation of 1-isobutyl-4-(1-methoxyethyl)benzene

Dry methanol (42.06 g, 1.31 mol, 5 eq.) and sulfuric acid (96%, 3.22 g, 0.032 mol, 0.12 eq.) were mixed. Dry 1-(4-isobutylphenyl)ethanol (93.6 GC-a %, 50 g, 0.263 mol, 1 eq.) was added dropwise over 15 minutes. After complete addition, the mixture was brought to reflux (56° C.). After 7 h at reflux, the reaction mixture was cooled to room temperature and 100 mL ethylacetate and subsequently 50 mL of saturated NaHCO₃-solution were added. The mixture was stirred for 5 min and then, the phases were separated. The organic phase was dried over Na₂SO₄ and filtered. Then, the solvent was removed under reduced pressure to give 48.5 g of the desired crude product in a purity of 88.2 GC-a % (2.3 GC-a % ethylacetate, 0.9 GC-a % staring material; 85% yield). The crude product was purified by fractional distillation (sump temperature 77-90° C., pressure 1.5-1.8 mbar). Fractions 4 and 5 were united which contained the desired product in >99 GC-a % purity. The product identity was confirmed via NMR $^{13}$C-NMR (125 MHz, CDCl₃): δ=140.9, 140.6, 129.1, 126.0, 79.5, 56.3, 45.1, 30.3, 23.8, 22.4.

3. Preparation of 1-isobutyl-4-(1-propoxyethyl)benzene

The process was carried out analogous to example 1, by using a solvent mixture of dry THF and DMSO and 1-iodopropane for the alkylation. An analytical sample was purified by column chromatography (SiO₂, gradient 5-20% ethylacetate in cyclohexane, 97% purity).

$^{13}$C-NMR (125 MHz, CDCl₃): δ=141.5, 140.7, 129.1, 125.9, 77.7, 70.3, 45.2, 30.3, 24.3, 23.2, 22.5, 10.7 ppm.

4. Preparation of 1-(1-butoxyethyl)-4-isobutylbenzene

The process was carried out analogous to the example 1, using 1-iodobutane for the alkylation. An analytical sample was purified by column chromatography (SiO₂, gradient 0-20% ethylacetate in cyclohexane, 95% purity).

$^{13}$C-NMR (125 MHz, CDCl₃): δ=141.5, 140.7, 129.1, 125.9, 77.8, 68.4, 45.2, 32.2, 30.3, 24.3, 22.5, 19.5, 14.0 ppm.

5. Preparation of 1-(1-isopropoxyethyl)-4-isobutylbenzene

Dry isopropanol (79.28 g, 1.32 mol, 5 eq.) and sulfuric acid (96%, 3.24 g, 0.032 mol, 0.12 eq.) were mixed. Dry 1-(4-isobutylphenyl)ethanol (94 GC-a %, 50 g, 0.264 mol, 1 eq.) was added dropwise over 15 minutes. After complete addition, the mixture was brought to reflux (78° C.). After 6.5 h at reflux, the reaction mixture was cooled to room temperature and 100 mL ethylacetate and subsequently 50 mL of saturated NaHCO₃-solution were added. The mixture was stirred for 5 min and then, the phases were separated. The organic phase was dried over Na₂SO₄ and filtered. Then, the solvent was removed under reduced pressure to give 51.2 g of the desired crude product in a purity of 82 GC-a % (5 GC-a % not converted starting material; 72% yield (not based on rec. starting material)). The crude product was purified by fractional distillation (sump temperature 94-115° C., pressure 1.9 mbar). Fractions 3, 4, 5 and 6 were united which contained the desired product in 92.9 GC-a % purity (and 3.2 GC-a % of starting material).

13C NMR (126 MHz, CDCl₃) δ 141.95, 140.57, 129.02, 129.02, 125.87, 125.87, 74.40, 68.26, 45.14, 30.24, 24.74, 23.33, 22.42, 22.42, 21.34.

1H NMR (500 MHz, Chloroform-d) δ 7.22 (d, J=8.0 Hz, 2H), 7.10 (d, J=8.0 Hz, 2H), 4.51 (q, J=6.5 Hz, 1H), 3.58-3.42 (m, 1H), 2.45 (d, J=7.2 Hz, 2H), 1.98-1.78 (m, 1H), 1.40 (d, J=6.5 Hz, 3H), 1.14 (d, J=6.1 Hz, 3H), 1.09 (d, J=6.3 Hz, 3H), 0.90 (d, J=6.7 Hz, 6H).

6. Preparation of 1-(1-isobutoxyethyl)-4-isobutylbenzene

Dry isobutanol (97.81 g, 1.32 mol, 5 eq.) and sulfuric acid (96%, 3.24 g, 0.032 mol, 0.12 eq.) were mixed. Dry 1-(4-isobutylphenyl)ethanol (94 GC-a %, 50 g, 0.264 mol, 1 eq.) was added dropwise over 15 minutes. After complete addition, the mixture was brought to reflux (92° C.). After 3 h at reflux, the reaction mixture was cooled to room temperature and 100 mL ethylacetate and subsequently 50 mL of saturated NaHCO₃-solution were added. The mixture was stirred for 5 min and then, the phases were separated. The organic phase (pH=3) was further washed with 120 mL of saturated NaHCO₃-solution. The organic phase (pH=7) was dried over Na₂SO₄ and filtered. Then, the solvent was removed under reduced pressure to give 60.8 g of the desired crude product in a purity of 85.2 GC-a % (1.5 GC-a % not converted starting material; 84% yield (not based on rec. starting material)). The crude product was purified by fractional distillation (sump temperature 102-125° C., pressure 1.6-1.7 mbar) and column chromatography. The desired product was obtained in 98.6 GC-a % purity.

13C NMR (126 MHz, CDCl₃) δ 141.56, 140.59, 129.02, 129.02, 125.88 125.88, 77.82, 75.55, 45.16, 30.24, 28.64, 24.18, 22.43, 22.42, 19.54, 19.48.

1H NMR (500 MHz, Chloroform-d) δ 7.20 (d, J=8.0 Hz, 2H), 7.10 (d, J=8.0 Hz, 2H), 4.34 (q, J=6.5 Hz, 1H), 3.05 (d, J=6.8 Hz, 2H), 2.46 (d, J=7.2 Hz, 2H), 1.84 (m, J=13.3, 6.7 Hz, 2H), 1.42 (d, J=6.3 Hz, 3H), 0.89 (dd, J=12.1, 6.7 Hz, 12H).

7. Preparation of 1-isobutyl-4-[(1R/1S)-1-[(1S)-1-methylpropoxy]ethyl]benzene Dry (S)-(+)-2-butanol (9.78 g, 0.13 mol, 5 eq.) and sulfuric acid (96%, 0.32 g, 0.003 mol, 0.12 eq.) were mixed. Dry 1-(4-isobutylphenyl)ethanol (94 GC-a %, 5 g, 0.026 mol, 1 eq.) was added drop-wise over 15 minutes. After complete addition, the mixture was brought to reflux (88° C.). After 2.5 h at reflux, the reaction mixture was cooled to room temperature and 10 mL ethylacetate and subsequently 10 mL of saturated NaHCO₃-solution were added. The mixture was stirred for 5 min and then, the phases were separated. The organic phase (pH=2) was further washed with 10 mL of saturated NaHCO₃-solution. The organic phase (pH=7) was dried over Na₂SO₄ and filtered. Then, the solvent was removed under reduced pressure to give 5.5 g of the desired crude product in a purity of 42.9 GC-a % diastereomer A or B and 39.6 GC-a % of the other diastereomer (diastereomer A or B) (4.1 GC-a % not converted starting material; 73% yield (not based on rec. starting material)). The crude product was purified by column chromatography. The desired product was obtained in 92.9 GC-a % purity.

Diastereomer A:

13C NMR (126 MHz, CDCl₃) δ 141.72, 140.63, 128.94, 128.94, 126.19 126.19, 74.25, 73.18, 45.14, 30.24, 30.24, 24.67, 22.50-22.30, 22.50-22.30, 18.88, 10.28.

1H NMR (500 MHz, Chloroform-d) δ 7.28-7.18 (m, 2H), 7.10 (d, J=7.5 Hz, 2H), 4.67-4.44 (m, 1H), 3.25-3.15 (m, J=6.1 Hz, 1H), 2.46 (d, J=7.2 Hz, 2H), 1.92-1.78 (m, J=13.5, 6.8 Hz, 1H), 1.62-1.27 (m, 5H), 1.12 (d, J=6.0 Hz, 3H), 0.90 (d, J=6.6 Hz, 6H), 0.80 (t, J=7.5 Hz, 3H).

Diastereomer B:

13C NMR (126 MHz, CDCl₃) δ 142.15, 140.56, 128.98, 128.98, 125.94, 125.94, 75.13, 73.86, 45.14, 30.24, 28.41, 24.32, 22.50-22.30. 22.50-22.30, 20.25, 9.49.

1H NMR (500 MHz, Chloroform-d) δ 7.28-7.18 (m, 2H), 7.10 (d, J=7.5 Hz, 2H), 4.60-4.44 (m, 1H), 3.37-3.28 (m, J=6.2 Hz, 1H), 2.46 (d, J=7.2 Hz, 2H), 1.92-1.78 (m, J=13.5, 6.8 Hz, 1H), 1.62-1.27 (m, 5H), 1.03 (d, J=6.3 Hz, 3H), 0.90 (m, 9H).

8. Preparation of 1-isobutyl-4-[(1R/1S)-1-[(1R)-1-methylpropoxy]ethyl]benzene Dry (R)-(−)-2-butanol (9.78 g, 0.13 mol, 5 eq.) and sulfuric acid (96%, 0.32 g, 0.003 mol, 0.12 eq.) were mixed. Dry 1-(4-isobutylphenyl)ethanol (94 GC-a %, 5 g, 0.026 mol, 1 eq.) was added drop-wise over 15 minutes. After complete addition, the mixture was brought to reflux (92° C.). After 3.5 h at reflux, the reaction mixture was cooled to room temperature and 10 mL ethylacetate and subsequently 10 mL of saturated NaHCO₃-solution were added.

The mixture was stirred for 5 min and then, the phases were separated. The organic phase (pH=7) was dried over Na₂SO₄ and filtered. Then, the solvent was removed under reduced pressure to give 4.4 g of the desired crude product in a purity of 40.2 GC-a % diastereomer A or B and 37.2 GC-a % of the other diastereomer (diastereomer A or B) (5.5 GC-a % not converted starting material; 55% yield (not based on rec. starting material)). The crude product was purified by column chromatography. The desired product was obtained in 98.9 GC-a % purity.

Diastereomer A

13C NMR (126 MHz, CDCl₃) δ 141.71, 140.63, 128.93, 128.93, 126.19, 126.19, 74.24, 73.18, 45.14, 30.23, 30.23, 24.66, 22.50-22.30, 22.50-22.30, 18.88, 10.27.

1H NMR (500 MHz, Chloroform-d) δ 7.36-7.15 (m, 2H), 7.10 (d, J=7.8 Hz, 2H), 4.65-4.33 (m, 1H), 3.25-3.15, (h, J=6.1 Hz, 1H), 2.46 (d, J=7.2 Hz, 2H), 1.85 (m, 1H), 1.61-1.28 (m, 5H), 1.12 (d, J=6.0 Hz, 3H), 0.89 (m, 6H), 0.80 (t, J=7.5 Hz, 3H).

Diastereomer B

13C NMR (126 MHz, CDCl₃) δ 142.15, 140.56, 128.98, 128.98, 125.93, 125.93, 75.12, 73.86, 45.14, 30.23, 28.41, 24.32, 22.50-22.30, 22.50-22.30, 20.25, 9.49.

1H NMR (500 MHz, Chloroform-d) δ 7.36-7.15 (m, 2H), 7.10 (d, J=7.8 Hz, 2H), 4.63-4.29 (m, 1H), 3.38-3.27 (m, 1H), 2.46 (d, J=7.2 Hz, 2H), 1.85 (m, 1H), 1.61-1.28 (m, 5H), 1.03 (d, J=6.3 Hz, 3H), 0.89 (m, 9H).

TABLE 1

Provides the aroma impression of compound of formula (I)

| Example No. | compound of formula (I) | Chemical name | Aroma impression |
|---|---|---|---|
| 1. | $R_1$ is —$CH_2CH_3$ | 1-(1-ethoxyethyl)-4-isobutylbenzene | watery, marine, mushroom, pungent, green and flowery |
| 2. | $R_1$ is —$CH_3$ | 1-isobutyl-4-(1-methoxyethyl)benzene | watery, sweet, rubbery, green, leafy, nutty |
| 3. | $R_1$ is —$CH_2CH_2CH_3$ | 1-isobutyl-4-(1-propoxyethyl)benzene | nutty, woody, dusty, rubbery, rooty, lemon |
| 4. | $R_1$ is —$CH_2CH_2CH_2CH_3$ | 1-(1-butoxyethyl)-4-isobutylbenzene | Rubbery, waxy |
| 5. | $R_1$ is —$CH(CH_3)_2$ | 1-(1-isopropoxyethyl)-4-isobutylbenzene | Floral, green, mushroom, muguet |
| 6. | $R_1$ is —$CH_2CH(CH_3)_2$ | 1-(1-isobutoxyethyl)-4-isobutylbenzene | nutty, woody, dusty, rubbery, rooty, lemon (less intense than ex.3) |
| 7. | $R_1$ is —$CH(CH_3)CH_2CH_3$ | 1-isobutyl-4-[(1R/1S)-1-[(1S)-1-methylpropoxy]ethydbenzene | nutty, woody, dusty, rubbery, rooty, lemon (less intense than ex. 3) |
| 8. | $R_1$ is —$CH(CH_3)CH_2CH_3$ | 1-isobutyl-4-[(1R/1S)-1-[(1R)-1-methyl propoxy]ethydbenzene | Floral, muguet, rubber |

The mixtures of compound of formula I with 4-methyl-2-(2-methylpropyl)oxan-4-ol (Pyranol) were evaluated for the aroma impression, TABLE 1a Provides the aroma impression of mixtures of compounds of formula (I) with 4-methyl 2-(2-methylpropyl)oxan-4-ol (Pyranol)

| No. | Mixture of | Concentration | Aroma impression |
|---|---|---|---|
| 1. | compound of formula (I) $R_1$ is —$CH_2CH_3$: 4-methyl-2-(2-methylpropyl)oxan-4-ol | 1:5 | Floral, muguet, powdery |
|  |  | 1:9 | Same as concentration of 1:5 |
|  |  | 1:20 | Same as concentration of 1:5 |
| 2. | compound of formula (I) $R_1$ is —$CH(CH3)_2$: 4-methyl-2-(2-methylpropyl)oxan-4-ol | 1:5 | Floral, muguet, powdery |
|  |  | 1:9 | Same as concentration of 1:5 |
|  |  | 1:20 | Same as concentration of 1:5 |

Compound A = any compound according to the table 1 or mixture according to table 1a Advantageous Fragrance Compositions Compound A as described above was formulated in the compositions according to tables 2 and 3. The amounts given in tables 2 and 3 are weight units in grams.

TABLE 2

Fragrance compositions 1A and 1B

|  | 1A | 1B |
|---|---|---|
| Lactone C10 gamma (5-hexyloxolan-2-one) | 2 | 2 |
| Bourgeonal (3-(4-tert-butylphenyl)propanal) | 2 | 2 |
| Citronellol | 3 | 3 |
| Aldehyde C-14 (5-heptyloxolan-2-one) | 3 | 3 |
| Allyl heptylate | 4 | 4 |
| Amber core (1-(2-tert-butylcyclohexyl)oxybutan-2-ol) | 4 | 4 |
| Ethyl-2-methyl butyrate | 4 | 4 |
| Geranyl acetate | 5 | 5 |
| Helional (3-(1,3-benzodioxol-5-yl)-2-methylpropanal) | 10 | 10 |
| Manzanate (ethyl 2-methylpentanoate) | 10 | 10 |
| Amberwood (ethoxymethoxycyclododecane) | 10 | 10 |
| Hexyl acetate | 11 | 11 |
| Benzyl salicylate | 12 | 12 |
| Magnolan (2,4-dimethyl-4,4a,5,9b-tetrahydroindeno[1,2-d][1,3]dioxine) | 15 | 15 |
| Verdox (2-tert-butylcyclohexyl) acetate) | 25 | 25 |
| Bergamot oil bergaptene free | 25 | 25 |
| Linalol | 30 | 30 |
| Dipropylene glycol | 45 | 45 |
| Iso E Super (Tetramethyl acetyloctahydronaphthalenes) | 110 | 110 |
| Pyranol (4-methyl-2-(2-methylpropyl)oxan-4-ol) | 170 | 170 |
| Hedione (methyl 3-oxo-2-pentylcyclopentaneacetate) | 200 | 200 |
| Galaxolide 50% IPM (1,3,4,6,7,8-hexahydro-4,6,6,7,8,8-hexamethylcyclopenta(g)-2-benzopyran 50% in isopropyl myristate) | 300 | 300 |
| Compound A | 5 | 100 |
|  | 1005 | 1100 |

TABLE 3

Fragrance compositions 2A and 2B

| | 2A | 2B |
|---|---|---|
| Raspberry ketone (4-(4-hydroxyphenyl)butan-2-one) | 4 | 4 |
| Vanitrope (2-ethoxy-5-prop-1-enylphenol) | 6 | 6 |
| Cyclamen aldehyde (at least 90% 2-methyl-3-(p-isopropylphenyl)propionaldehyde; secondary component: 5% 3-(p-cumenyl)-2-methylpropionic acid) | 10 | 10 |
| Bicyclononalactone (3,4,4a,5,6,7,8,8a-octahydrochromen-2-one) | 10 | 10 |
| Aldehyde C-14 (5-heptyloxolan-2-one) | 14 | 14 |
| Ethylvanillin (3-ethoxy-4-hydroxybenzaldehyde) | 16 | 16 |
| Heliotropine (1,3-benzodioxole-5-carbaldehyde) | 20 | 20 |
| iso E Super (tetramethyl acetyloctahydronaphthalenes) | 20 | 20 |
| Sandela (3[5,5,6-trimethylbicyclo[2.2.1]hept-2-yl]cyclohexan-1-ol) | 30 | 30 |
| Vanillin isobutyrate ((4-formyl-2-methoxyphenyl) 2-methylpropanoate) | 40 | 40 |
| Aldehyde C-18 (5-pentyloxolan-2-one) | 50 | 50 |
| Benzyl salicylate | 60 | 60 |
| Hexyl cinnamic aldehyde (2-(phenylmethylidene)octanal) | 70 | 70 |
| Hedione (methyl 3-oxo-2-pentylcyclopentaneacetate) | 130 | 130 |
| Pyranol (4-methyl-2-(2-methylpropyl)oxan-4-ol) | 150 | 150 |
| Ethylene brassylate (1,4-dioxacycloheptadecane-5,17-dione) | 170 | 170 |
| Galaxolide 50% IPM (1,3,4,6,7,8-hexahydro-4,6,6,7,8,8-hexamethylcyclopenta(g)-2-benzopyran 50% in isopropyl myristate) | 200 | 200 |
| Compound A | 5 | 50 |
| | 1005 | 1050 |

Composition according to table 2 and table 3 namely 1A, 1B, 2A, 2B could be included in various compositions selected from the group consisting of Deo pump spray, Clean hair-conditioner, Face wash gel, Foam bath concentrate, Hair gel, Self-foaming bodywash, Sprayable sun care emulsion, Sprayable sun protection emulsion, Emollient facial gel, 2-phases oil foam bath, Shampoos, Shower bath, Hydro-alcoholic AP/Deo pump spray, Aerosol, Aqueous/alcoholic AP/Deo roll-on, Styling Gel Type "Out of Bed", Shaving Foam, Sensitive skin Baby shampoo, Body wash for Sensitive Skin, Gloss Enhancing Shampoo for Sensitive Scalp, Deo Stick, Baby Wipe, After shave balm, Face Gel, Face Day Care Cream, Face Cleanser, Body lotion, Sun Care SPF50+, Sprayable Lotion, Hand dish cleaner—regular, Hand dish cleaner—concentrate, Sanitary cleaner—concentrate, All-purpose cleaner, Antibacterial fabric softener, Detergent composition, Powder detergent composition and Liquid detergent composition.

A person skilled in art may be well versed with the various general formulations for the above-mentioned products.

Compositions 1A, 1B, 2A and 2B can for example be formulated in specific formulations as disclosed in IP.com Number: IPCOM000258614D entitled New Aroma Chemicals pages 6 to 46, Table 1 to Table D13, wherein the "Fragrance Composition 1A" is replaced by identical amounts of compositions 1A, 1B, 2A or 2B.

The invention claimed is:

1. Method of imparting an aroma impression to a composition comprising at least the step of adding a compound of formula (I),

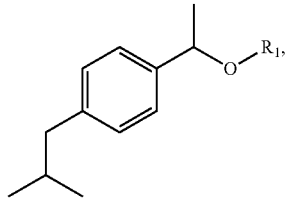

formula (I)

wherein
R$_1$ is selected from the group consisting of linear or branched, unsubstituted —C$_1$-C$_5$ alkyl and unsubstituted —C$_3$-C$_5$ cycloalkyl;
or its salt or stereoisomer thereof,
to a composition.

2. The method according to claim 1, wherein R$_1$ is selected from the group consisting of —CH$_3$, —CH$_2$CH$_3$, —CH$_2$CH$_2$CH$_3$, —CH(CH$_3$)$_2$, —CH(CH$_3$)(C$_2$H$_5$), —CH$_2$CH(CH$_3$)$_2$, —CH$_2$CH$_2$CH$_2$CH$_3$, —CH(CH$_3$)$_2$, —CH$_2$CH(CH$_3$)$_2$, —CH(CH$_3$) CH$_2$CH$_3$, —CH(CH$_3$) CH$_2$CH$_3$, and cyclopropyl.

3. The method according to claim 1, wherein the composition is selected from the group consisting of perfume compositions, body care compositions, hygiene articles, cleaning compositions, textile detergent compositions, compositions for scent dispensers, foods, food supplements, pharmaceutical compositions, and crop protection compositions.

4. The method according to claim 1, wherein the impression is selected from a group consisting of a flowery note, a marine note, a sweet note, a rubbery note, a nutty note, a woody note, a dusty note, a rooty note, a lemon note, and a green note.

5. The method according to claim 1, wherein the compound of formula (I) or its salts or stereoisomer is present in an amount in the range of ≥0.01 wt. % to ≤70.0 wt. %, based on the total weight of the composition.

6. A composition comprising at least one compound of the formula (I),

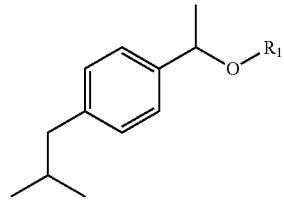

formula (I)

wherein
R$_1$ is selected from the group consisting of linear or branched, unsubstituted —C$_2$-C$_5$ alkyl and unsubstituted —C$_3$-C$_5$ cycloalkyl;
or its salt or stereoisomer thereof and
(i) at least one aroma chemical, or
(ii) at least one non-aroma chemical carrier, or
(iii) both of (i) and (ii).

7. The composition according to claim 6, wherein R$_1$ is selected from the group consisting of —CH$_2$CH$_3$, —CH$_2$CH$_2$CH$_3$, —CH(CH$_3$)$_2$, —CH(CH$_3$)(C$_2$H$_5$), —CH$_2$CH(CH$_3$)$_2$, —CH$_2$CH$_2$CH$_2$CH$_3$, —CH(CH$_3$)$_2$, —CH$_2$CH(CH$_3$)$_2$, —CH(CH$_3$) CH$_2$CH$_3$, cyclopropyl, and cyclobutyl.

8. The composition according to claim 6, wherein the at least one non-aroma chemical carrier (ii) is selected from the group consisting of surfactants, oil components, antioxidants, deodorant-active agents, and solvents.

9. The composition according to claim 6, wherein the composition is selected from the group consisting of perfume compositions, body care compositions, hygiene articles, cleaning compositions, textile detergent compositions, compositions for scent dispensers, foods, food supplements, pharmaceutical compositions, and crop protection compositions.

10. A mixture comprising compound of formula (I),

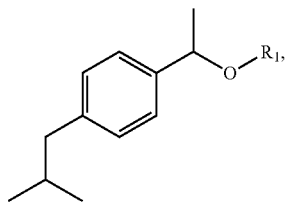

formula (I)

wherein
$R_1$ is selected from the group consisting of linear or branched, unsubstituted —$C_1$-$C_5$ alkyl and unsubstituted —$C_3$-$C_5$ cycloalkyl;
or its salt or stereoisomer thereof; and
4-methyl-2-(2-methylpropyl) oxan-4-ol.

11. The mixture according to claim 10, wherein $R_1$ is selected from the group consisting of —$CH_3$, —$CH_2CH_3$, —$CH_2CH_2CH_3$, —$CH(CH_3)_2$, —$CH(CH_3)(C_2H_5)$, —$CH_2CH(CH_3)_2$, —$CH_2CH_2CH_2CH_3$, —$CH(CH_3)_2$, —$CH_2CH(CH_3)_2$, —$CH(CH_3)$ $CH_2CH_3$ and cyclopropyl.

12. A method for imparting an aroma impression to a composition, comprising adding the mixture according to claim 10, to the composition.

13. A composition comprising,
(i) the mixture according to claim 10, and
(ii) at least one aroma chemical, or
(iii) at least one non-aroma chemical carrier, or
(iv) both of (ii) and (iii).

14. A compound of formula (I'),

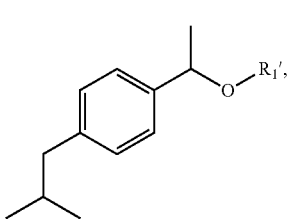

formula (I')

wherein
$R_1'$ is selected from the group consisting of linear or branched-$CH_2CH_2CH_3$, —$CH(CH_3)(C_2H_5)$, —$CH_2CH(CH_3)_2$, —$CH(CH_3)$ $CH_2CH_3$ and —$CH_2CH_2CH_2CH_3$;
or its salt or stereoisomer thereof.

* * * * *